United States Patent [19]

Carlsson et al.

[11] 4,263,323

[45] Apr. 21, 1981

[54] β-RECEPTOR BLOCKING COMPOUNDS AND TREATMENT OF CARDIOVASCULAR DISORDERS THEREWITH

[75] Inventors: Enar I. Carlsson, Västra Frölunda; Gustav B. R. Samuelsson, Mölnlycke; Bo T. Lundgren, Frillesås, all of Sweden

[73] Assignee: Aktiebolaget Hässle, Mölndal, Sweden

[21] Appl. No.: 27,279

[22] Filed: Apr. 5, 1979

Related U.S. Application Data

[62] Division of Ser. No. 839,636, Oct. 5, 1977, abandoned.

[51] Int. Cl.³ .................. A61K 31/165; C07C 103/26; C07C 103/28
[52] U.S. Cl. .................. 424/324; 564/162; 564/165
[58] Field of Search .......... 260/559 T, 559 A, 559 D; 424/324

[56] References Cited

U.S. PATENT DOCUMENTS

| 3,192,253 | 6/1965 | Boscott et al. .............. 424/330 |
| 4,027,027 | 5/1977 | Jaeggi et al. ............... 424/266 |

FOREIGN PATENT DOCUMENTS

| 902617 | 8/1962 | United Kingdom . |
| 1245148 | 9/1971 | United Kingdom ............ 424/330 |
| 1326961 | 8/1973 | United Kingdom . |
| 1433920 | 4/1976 | United Kingdom . |

Primary Examiner—Anna P. Fagelson
Attorney, Agent, or Firm—Brumbaugh, Graves, Donohue & Raymond

[57] ABSTRACT

Amines of the formula I

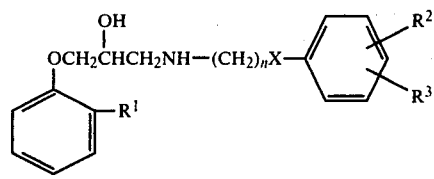

method of preparing the same and pharmaceutical compositions and method for treating cardiovascular disorders by blocking the β-receptors of the heart in combination with a peripheral vasodilating activity.

6 Claims, No Drawings

β-RECEPTOR BLOCKING COMPOUNDS AND TREATMENT OF CARDIOVASCULAR DISORDERS THEREWITH

This is a division and continuation-in-part of our copending application Ser. No. 839,636 filed October 5, 1977, now abandoned.

The present invention relates to new potent β-receptor blocking compounds as well as their preparation and a method for treating symptoms and signs of cardiovascular disorders by blocking the β-receptors of the heart by administering to mammals, including man, these new compounds.

The new compounds are those of the general formula

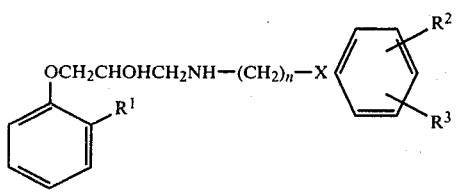

wherein $R^1$ is selected from the group consisting of methyl, ethyl, propyl, methoxy, propargyloxy, cyano, allyloxy, acetyl, cyanomethyl, hydroxymethyl, $CH_3OC_2H_4NHCOCH_2O-$, morpholino, pyrrolidino and pyrrolyl, $R^2$ and $R^3$ are the same or different and are each selected from the group consisting of hydrogen, alkoxyalkoxy, alkyl, cyano hydroxy, halogen, alkoxy, and hydroxymethyl provided that $R^2$ and $R^3$ are not both hydrogen, n is an integer 2, 3, or 4, and X is —O— or —S—.

Preferably $R^1$ is $CH_3OC_2H_4NHCOCH_2O$.

n is an integer 2, 3, or 4, preferably 2.

X is oxygen or sulphur, preferably oxygen.

$R^2$ and $R^3$ are bound in the 2-, 3-, or 4-position and preferably bound in the 3- or 4-position to the alkylene side chain on the phenoxy or phenylthio group, whereby preferably $R^2$ is hydrogen and $R^3$ is hydroxy, $R^2$ and $R^3$ are 3,4-dimethoxy, $R^2$ and $R^3$ are 3,4-dichloro, $R^2$ is chloro and $R^3$ is hydroxy.

The new compounds have valuable pharmacological properties. Thus they block cardiac β-receptors, which is shown at the determination of the antagonism of tachycardia after an intravenous injection of 0.1 ug/kg of 1-isoproterenol sulphate on an anaesthetized cat at an intravenous dose of 0.012–51.2 umol/kg. The compounds are heart selective with regard to their β-blocking activity.

The new compounds can be used at the treatment of arrythmias, angina pectoris and hypertension. One may also use them as intermediates in the preparation of other valuable pharmaceutical compounds.

Compounds according to the present invention are: 3-[2-(4-hydroxyphenoxy)ethylamino]-1-o-methoxyethylaminocarbonylmethoxyphenoxy-propanol-2

Salt forming acids may be used in preparing therapeutically acceptable salts of the compounds. These are: hydrohalogen acids, sulfuric acid, phosphoric acid, nitric acid, perchloric acid, aliphatic, alicyclic, aromatic or heterocyclic carboxy or sulfonic acids, such as formic, acetic, propionic, succinic, glycolic, lactic, malic, tartaric, citric, ascorbic, maleic, hydroxymaleic, or pyrovic acid, phenylacetic, benzoic, p-aminobenzoic, anthranilic, p-hydroxybenzoic, salicyclic or p-aminosalicyclic acid, embonic acid, methanesulfonic, hydroxyethane sulfonic, ethylenesulfonic, halogenbenzenesulfonic, toluenesulfonic, naphthylsulfonic, or sulfanilic acid, methionine, tryptophane, lysine or arginine.

The substances are intended to be administered orally or parenterally for acute and chronic treatment of the above mentioned cardiovascular disorders.

The biological effects of the new compounds have been tested, and the different tests carried out will be shown and explained below.

The new compounds are obtained according to methods known per se. Thus, a compound of formula II

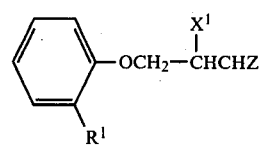

wherein $R^1$ has the meaning given above. $X^1$ is a hydroxy group, Z is a reactive, esterified hydroxy group, or $X^1$ and Z together form an epoxy group, is reacted with an amine of the formula

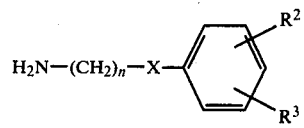

wherein $R^2$, $R^3$, n and X have the same meanings as given above.

A reactive, esterified hydroxy group is particularly an hydroxy group esterified with a strong, inorganic or organic acid, preferably a hydrohalogen acid, as hydrochloric acid, hydrobromic acid, or hydroiodic acid, further sulfuric acid or a strong organic sulfonic acid, e.g. benzenesulfonic acid, 4-bromobenzenesulfonic acid, or 4-toluenesulfonic acid. Thus, Z is preferably chloro, bromo or iodo.

This reaction is carried out in a common way. With the use of a reactive ester as a starting material the preparation takes place preferably in the presence of a basic condensating agent and/or with an excess of an amine. Suitable basic condensating agents are e.g. alkalimetal hydroxides as sodium or potassium hydroxide, alkalimetal carbonates as potassium carbonate and alkalimetal alcoholates as sodium methylate, potassium ethylate and potassium tert.-butylate.

The reaction is carried out in an alkanol having 1 to 4 carbon atoms by refluxing the reactants in said solvent for a time long enough to give the compound of formula I, generally 1 to 12 hrs.

Further, a compound of formula III

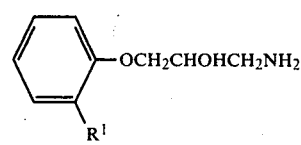

wherein $R^1$ has the meaning given above, is reacted with a compound of the formula

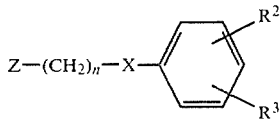

wherein $R^2$, $R^3$, n, X, and Z have the same meanings as given above.

This reaction is carried out in a common way, preferably in the presence of a basic condensating agent and/or an excess of an amine. Suitable basic condensating agents are e.g. alkaline alcoholates, preferably sodium or potassium alcoholate, or also alkaline carbonates as sodium or potassium carbonate.

This reaction is carried out in an alkanol having 1 to 3 carbon atoms in an autoclave being heated to 100° to 130° C. for 5 to 15 hrs.

Further, a compound of formula IV

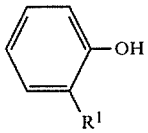
(IV)

wherein $R^1$ has the same meaning as given above is reacted with a compound of formula V

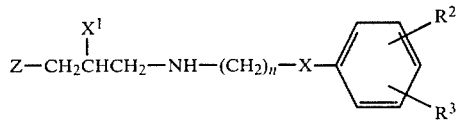
(V)

wherein Z, $X^1$, $R^2$, $R^3$, n and X have the same meanings as given above.

This reaction is carried out in a common way. In those cases where reactive esters are used as starting material, the compound of formula IV may suitably be used in the form of its metalphenolate as alkalimetalphenolate, preferably sodiumphenolate, or one works in the presence of an acid binding agent, preferably a condensating agent, which can form a salt of the compound of formula IV as an alkalimetal alcoholate.

This reaction is carried out in an alkanol having 1 to 3 carbon atoms in an autoclave being heated to 80° to 100° C. for 5 to 15 hrs.

Further, a compound of formula Va

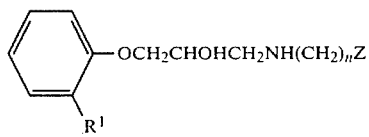
(Va)

wherein $R^1$, Z and n have the meanings given above, is reacted with a compound of formula IVa

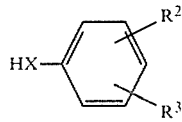
(IVa)

wherein $R^2$, $R^3$ and X have the same meanings as given above.

This reaction is carried out in the same way as the reaction between compounds of formula IV and V above.

Further, a compound of formula IV

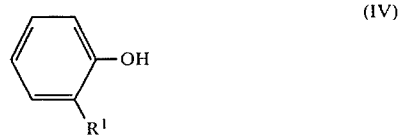
(IV)

wherein $R^1$ has the same meaning as given above, is reacted with a compound of formula VI

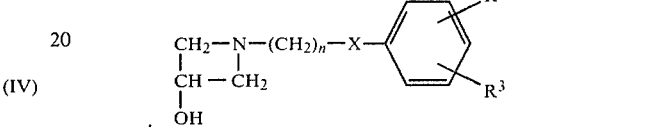
(VI)

wherein $R^2$, $R^3$, n and X have the same meanings as given above.

This reaction is carried out in a common way. Thus, the reaction is carried out under alkaline conditions in a suitable solvent, as benzylalcohol by boiling the reaction mixture for some hours. Thereby the phenol is primarily converted to its metalphenolate as alkalimetalphenolate before it is added to the acetidinol of formula VI.

Further, one may split off a residue from a compound of formula I above, in which the nitrogen atom of the amino group and/or the hydroxy groups have attached thereto a splitable residue.

Such splitable residues are especially those which are splitable by solvolysis, reduction, pyrolysis or fermentation.

Residues splitable by solvolysis are preferably residues splitable by hydrolysis or ammonolysis.

Residues splitable by means of hydrolysis are e.g. an acyl residue, which, when present, are functionally varied carboxy groups, e.g. oxycarbonyl residues, as alkoxycarbonyl residues, e.g. tert.-butoxycarbonyl residue, or ethoxycarbonyl residue, aralkoxycarbonyl residues as phenylloweralkoxycarbonyl residues, e.g. a carbobenzyloxy residue halogencarbonyl residue, e.g. a chlorocarbon residue further arylsulphonyl residues as toluenesulfonyl or bromobenzenesulfonyl residues and possibly as halogenated, as fluorinated loweralkanoyl residues as formyl-, acetyl- or trifluoroacetyl residues or a benzyl residue or cyano groups or silyl residues, as trimethylsilyl residue.

Of the above mentioned residues present at the hydroxy groups, which residues are splitable by hydrolysis, preferably the oxycarbonyl residues and the loweralkanoyl residues or the benzoyl residues are used.

Besides the above mentioned also double-bound residues, which are splitable at the amino group by hydrolysis are used, e.g. alkylidene or benzylidene residue or a phosphorylidene group as a triphenylphosphorylidene group, whereby the nitrogen atom then obtains a positive charge.

Residues splitable at the hydroxy group and the amino group by hydrolysis are furthermore divalent residues as in occurring cases substituted methylene. As substituents on the methylene residues any organic residue may be used, whereby it does not matter at the hydrolysis which compound is the substituent to the methylene residue. As methylene substituents e.g. aliphatic or aromatic residues as alkyl as mentioned above, aryl-aryl e.g. phenyl or pyridyl may be used. The hydrolysis may be carried out in any common way, suitably in a basic or preferably in an acid medium.

Compounds having residues being splitable by hydrolysis are also the compounds according to formula VII

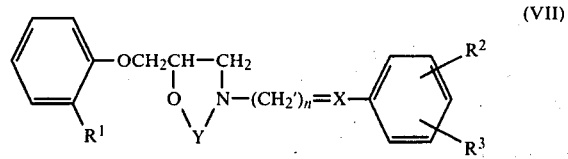

wherein $R^1$, $R^2$, $R^3$, n and X have the same meanings as given above and Y is a carbonyl or thiocarbonyl residue.

The hydrolysis is carried out in an analogous way, e.g. in the presence of a hydrolysing agent, e.g. in the presence of an acidic agent as e.g. diluted mineral acids, as sulfuric acid or hydrohalogen acid, or in the presence of basic agents as e.g. alkalimetal hydroxides, as sodium hydroxide. Oxycarbonyl residues, aryl sulfonyl residues and cyano groups may in a suitable way be split off by means of acidic agents as by means of a hydrohalogen acid, suitably hydrobromic acid. Preferably the splitting may take place using diluted hydrobromic acid, possibly in a mixture with acetic acid. Cyano groups are preferably split off by means of hydrobromic acid at an elevated temperature, as in boiling hydrobromic acid, according to the "bromocyano method" (v. Braun). Further, e.g. a tert.-butoxycarbonyl residue may be split off under anhydrous conditions by means of a treatment with a suitable acid, as trifluoracetic acid. Acidic agents are preferably used at a hydrolysis of compounds of formula VI.

Residues splitable by ammonolysis are especially the halogencarbonyl residues, as the chlorocarbonyl residue. The ammonolysis may be carried out in a common way, e.g. by means of an amine containing at least one hydrogen atom bounded to the nitrogen atom, as a mono- or diloweralkylamine e.g. methylamine or dimethylamine, or especially ammonia, preferably at an elevated temperature. Instead of ammonia one may use an agent which gives ammonia as hexamethylene tetraamine.

Residues splitable by means of a reduction are e.g. an α-arylalkyl residue, as a benzyl residue or an α-aralkoxycarbonyl residue as a benzyloxycarbonyl residue, which in a common way may be split off by means of a hydrogenolysis, especially by catalytically activated hydrogen, as by hydrogen in the presence of hydrogenating catalysts, e.g. Raney-nickel. Further residues splitable by means of hydrogenolysis are 2-halogenalkoxycarbonyl residues as 2,2,2-trichloroethoxycarbonyl residues or 2-iodoethoxy- or 2,2,2-tri-bromoethoxycarbonyl residues, which may be split off in a common way, suitably by means of a metallic reduction (so called nascerating hydrogen). Nascerating hydrogen may be obtained by the influence of metal or metal alloys, as amalgam on compounds which give hydrogen as carboxy acids, alcohols or water, whereby especially zink or zinkalloys together with acetic acid may be used. Hydrogenolysis of 2-halogenalkoxycarbonyl residues may further take place using chromium or chromium (II) compounds as chromium (II) chloride or chromium (II) acetate.

A residue splitable by reduction may also be an arylsulfonyl group as a toluenesulfonyl group, which in a common way may be split off by reduction using nascerating hydrogen, e.g. by means of an alkalimetal, as lithium or sodium in liquid ammonia, and suitably may be split off from a nitrogen atom. At the carrying out of the reduction one has to take care of the fact that other reducing groups are not influenced.

Residues splitable by means of pyrolysis, especially residues splitable from the nitrogen atom, are in occurring cases substituted suitably unsubstituted carbamoyl groups. Suitable substituents are e.g. loweralkyl or arylloweralkyl as methyl or benzyl or aryl, as phenyl, the pyrolysis is carried out in a common way, whereby one may have to take care of other thermically susceptible groups.

Residues splitable by means of fermentation, especially residues splitable from the nitrogen atom are in occurring cases substituted, however suitably unsubstituted carbamoyl groups. Suitable substituents are e.g. loweralkyl or arylloweralkyl, as methyl or benzyl, or aryl as phenyl. The fermentation is carried out in a common way, e.g. by means of the enzyme urease or soy bean extract at about 20° C. or slightly elevated temperature.

Further, a Schiff's base of formula VIII or IX

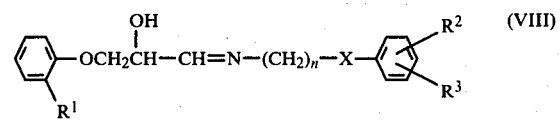

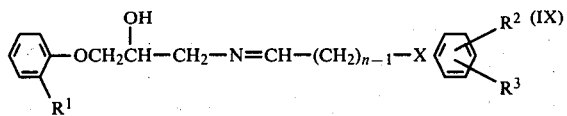

or a cyclic tautomer corresponding to formula IX or formula X

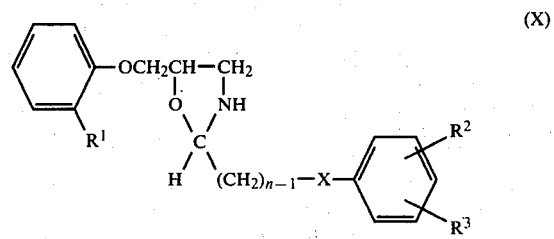

can be reduced, wherein $R^1$, $R^2$, $R^3$, n and X have the same meanings as given above, and whereby the compounds of formula IX and X may exist together, too. This reduction is carried out in a common way, e.g. using a di-lightmetalhydride, as sodiumborohydride, lithiumaluminiumhydride, using a hydride as Boran with formic acid, or by means of a catalytic hydrogenation, as with hydrogen in the presence of Raney-nickel. At the reduction one has to take care of the fact that other groups are not affected.

Further, the oxo group in the compound of formula XI

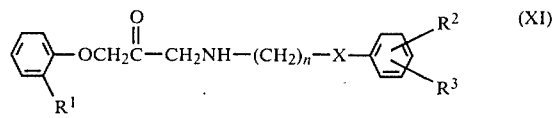

wherein $R^1$, $R^2$, $R^3$, n and X have the same meanings as given above, can be reduced to a hydroxy group. This reduction is carried out in a common way, especially using a di-lightmetalhydride, as mentioned above, or according to the "Meerwein-Pondorf-Verley method" or a modification thereof, suitably using an alkanol as a reaction component and as solvent, as isopropanol, and using a metalalkanolate, as metalisopropanolate, e.g. aluminium isopropanolate.

Further, in a compound of formula XII

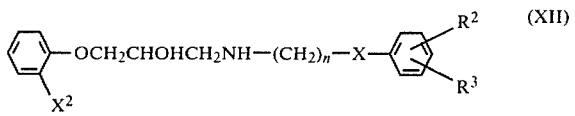

wherein $R^2$, $R^3$, n and X have the same meanings as given above, and wherein $X^2$ is a residue, which is able to be transformed to a residue $R^1$, one transforms $X^2$ to $R^1$.

Further, the oxo group in a compound corresponding to these of formula I and which carries an oxo group at a carbon atom bound to a nitrogen atom may be reduced by two hydrogen atoms.

Said compounds are e.g. such of the formula XIII

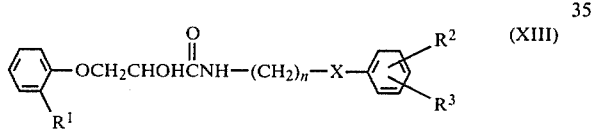

wherein $R^1$, $R^2$, $R^3$, n and X have the meaning as given above.

The reduction can be carried out according to the above described manner using complex metalhydrides, e.g. lithiumaluminiumhydride or di-isobutylaluminiumhydride. Suitably the reaction takes place in an inert solvent as an ether, e.g. diethylether or tetrahydrofuran.

Depending on the process conditions and the starting material the end product is obtained either in free form or in the form of its acid addition salt, which is included in the scope of the invention. Thus, for example, basic, neutral or mixed salts may be obtained as well as hemiamino, sesqui- or polyhydrates. The acid addition salts of the new compounds may in a manner known per se be transformed into free compounds using e.g. basic agents as alkali or ion exchanger. On the other hand, the free bases obtained may form salts with organic or inorganic acids. In the preparation of acid addition salts preferably such acids are used which form suitable therapeutically acceptable salts. Such acids are e.g. hydrohalogen acids, sulfuric acid, phosphoric acid, nitric acid, perchloric acid, aliphatic, alicyclic, aromatic or heterocyclic, carboxy or sulfonic acids, as formic, acetic, propionic, succinic, glycolic, lactic, malic, tartaric, citric, ascorbic, maleic, hydroxymaleic or pyruvic acid, phenylacetic, benzoic, p-aminobenzoic, anthranilic, p-hydroxybenzoic, salicyclic or p-aminosalicyclic acid, embonic acid, methanesulfonic, ethanesulfonic, hydroxyethanesulfonic, ethylenesulfonic acids, halogenbenzenesulfonic, toluenesulfonic, naphtylsulphonic acids, or sulfanilic acid; methionine, tryptophane, lysine or arginine.

These or other salts of the new compounds as e.g. picrates may serve as purifying agents or the free bases obtained as the free bases are transformed into salts, these are separated and the bases are then set free from the salts again. According to the close relationship between the new compounds in free form and in the form of their salts it will be understood from the above and the below that, if possible, the corresponding salts are included in the free compound.

The invention also relates to any embodiment of the process of which one starts from any compound obtained as an intermediate in any process step and one carries out the lacking process step, or one breaks off the process at any step, or at which one forms a starting material under the reaction conditions, or at which a reaction component possibly in the form of its salt is present.

Thus, one may react an aldehyde of the formula XIX

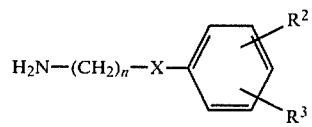

wherein $R^1$ has the same meaning as given above, with an amine of the formula

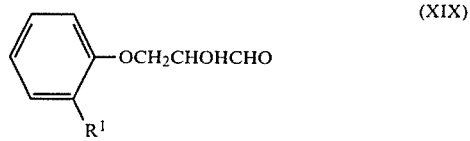

wherein $R^2$, $R^3$, n and X have the same meaning as given above, in the presence of a suitable reducing agent, as one of the above mentioned. Thereby a compound of formula VII is obtained as an intermediate, which then is reduced according to the invention.

Further, one may in a manner known per se react an amine of the formula III with an aldehyde or a keton of the formula

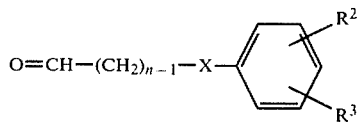

in the presence of a suitable reducing agent, as one of the above mentioned to produce compounds of formula IX or X as an intermediate, which then is reduced according to the invention.

The new compounds may, depending on the choice of starting materials and process, be present as optical antipodes or racemate, or, if they contain at least two asymmetric carbon atoms, be present as an isomer mixture (racemate mixture).

The isomer mixtures (racemate mixtures) obtained may, depending on physical-chemical differences of the component, be separated into the both stereoisomeric (diastereomeric) pure racemate e.g. by means of chromatography and/or fractionated crystallization.

The racemates obtained can be separated according to known methods, e.g. by means of recrystallization from an optical active solvent, by means of microorganisms, or by a reaction with optically active acids forming salts of the compound and separating the salts thus obtained, e.g. by means of their different solubility in the diastereomeres, from which the antipodes by the influence of a suitable agent may be set free. Suitably useable optically active acids are e.g. the L- and D-forms of tartaric acid, di-o-tolyltartaric acid, malic acid, mandelic acid, camphersulfonic acid or china acid. Preferably the more active part of the two antipodes is isolated.

Suitably such starting materials are used for carrying out the reactions of the invention, which material leads to groups of end products primarily especially desired and especially to the specifically described and preferred end products.

The starting materials are known or may, if they should be new, be obtained according to processes known per se.

In clinical use the compounds of the invention are administered normally orally, rectally or by injection in the form of a pharmaceutical preparation, which contains an active component either as free base or as pharmaceutically acceptable, non-toxic acid addition salts, e.g. the hydrochloride lactate, acetate, sulphamate or the like in combination with a pharmaceutical carrier. Thereby the mentioning of the new compounds of the invention is here related to either the free amine base or the acid addition salts of the free base, even if the compounds are generally or specifically described, provided that the context in which such expressions are used, e.g. in the examples, with this broad meaning should not correspond. The carrier may be a solid, semisolid or liquid diluent or a capsule. These pharmaceutical preparations are a further object of the invention. Usually the amount of active compound is between 0.1 to 99% by weight of the preparation, suitably between 0.5 to 20% by weight in preparations for injection and between 2 to 50% by weight in preparations for oral administration.

In the preparation of pharmaceutical preparations containing a compound of the present invention in the form of dosage units for oral administration the compound elected may be mixed with a solid, pulverulent carrier, as e.g. with lactose, saccharose, sorbitol, mannitol, starch, as potatoe starch, corn starch, amylopectin, cellulose derivatives or gelatine, as well as with an antifriction agent as magnesium stearate, calcium stearate, polyethyleneglycol waxes or the like, and be pressed into tablets. If coated tablets are wanted, the above prepared core may be coated with concentrated solution of sugar, which solution may contain e.g. gum arabicum, gelatine, talc, titandioxide or the like. Furthermore, the tablets may be coated with a laquer dissolved in an easily volatile organic solvent or mixture of solvents. To this coating a dye may be added in order to easily distinguish between tablets with different active compounds or with different amounts of the active compound present.

In the preparation of soft gelatine capsules (pearl-shaped, closed capsules), which consist of gelatine and e.g. glycerine or in the preparation of similar closed capsules the active compound is mixed with a vegetable oil. Hard gelatine capsules may contain granules of the active compound in combination with a solid, pulverulent carrier as lactose, saccharose, sorbitol, mannitol, starch (as e.g. potatoe starch, corn starch or amylopectin), cellulose derivatives or gelatine.

Dosage units for rectal administration may be prepared in the form of suppositories, which contain the active substance in a mixture with a neutral fat base, or they may be prepared in the form of gelatine-rectal capsules which contain the active substance in a mixture with a vegetable oil or paraffin oil.

Liquid preparations for oral administration may be present in the form of sirups or suspensions, e.g. solutions containing from about 0.2% by weight to about 20% by weight of the active substance described, whereby the residue consists of sugar and a mixture of ethanol, water, glycerol and propylene glycol. If desired, such liquid preparations may contain colouring agents, flavouring agents, saccharine and carboxymethylcellulose as a thickening agent.

Solutions for parenteral administration by injection may be prepared as an aqueous solution of a watersoluble pharmaceutically acceptable salt of the active compound, preferably in a concentration from about 0.5% by weight to about 10% by weight. These solutions may also contain stabilizing agents and/or buffering agents and may suitably be available in different dosage unit ampoules.

The preparation of pharmaceutically tablets for peroral use is carried out in accordance with the following method:

The solid substances included are ground or sieved to a certain particle size. The binding agent is homogenized and suspended in a certain amount of solvent. The therapeutic compound and necessary auxiliary agents are mixed during a continuous and constantly mixing with the binding agent solution and are moistened so that the solution is uniformly divided in the mass without overmoistening any parts. The amount of solvent is usually so adapted that the mass obtains a consistency reminding of wet snow. The moistening of the pulverulent mixture with the binding agent solution causes the particles to gather together slightly to aggregates and the real granulating process is carried out in such a way that the mass is pressed through a sieve in the form of a net of stainless steel having a mesh size of about 1 mm. The mass is then placed in thin layers on a tray to be dried in a drying cabinet. This drying takes place during 10 hours and has to be standardized carefully as the damp degree of the granulate is of utmost importance for the following process and for the feature of the tablets. Drying in a fluid bed may possibly be used. In this case the mass is not put on a tray but is poured into a container having a net bottom.

After the drying step the granules are sieved so that the particle size wanted is obtained. Under certain circumstances powder has to be removed.

To the so called final mixture, disintegrating, antifriction agents and antiadhesive agents are added. After this mixture the mass shall have its right composition for the tabletting step.

The cleaned tablet punching machine is provided with a certain set of punches and dies, whereupon the suitable adjustment for the weight of the tablets and the degree of compression is tested out. The weight of the tablet is decisive for the size of the dose in each tablet and is calculated starting from the amount of therapeutic agent in the granules. The degree of compression affects the size of the tablet, its strength and its ability of disintegrate in water. Especially as regards the two later properties the choice of compression pressure (0.5 to 5 ton) means something of a balance-step. When the right adjustment is set, the preparation of tablets is started which is carried out with a rate of 20,000 to 200,000 tablets per hour. The pressing of the tablets requires different times and depends on the size of the batch.

The tablets are freed from adhering pulver in a specific apparatus and are then stored in closed packages until they are delivered.

Many tablets, especially these which are rough or bitter, are coated with a coating. This means that these are coated with a layer of sugar or some other suitable coating.

The tablets are usually packed by machines having an electronic counting device. The different types of packages consist of glass or plastic gallipots but also boxes, tubes and specific dosage adapted packages.

The daily dose of the active substance varies and is depending on the type of administration, but as a general rule it is 100 to 400 mg/day of active substance at peroral administration and 5 to 20 mg/day at intravenous administration.

The following illustrates the principle and the adaption of the invention, however, without being limited thereto. Temperature is given in degrees Celsius.

EXAMPLE 1

Preparation of 3-[2-(4-hydroxyphenoxy)-ethylamino]-1-o-methylphenoxy-propanol-2

2.5 g of 1,2-epoxy-3-o-methylphenoxy propane were mixed with 1.5 g of 2-(4-hydroxyphenoxy)-ethylamine and 25 ml of isopropanol and the total solution was refluxed for 1.5 hours. The solution was thereupon evaporated in vacuo. The base thus obtained was dissolved in acetone and the hydrochloride was precipitated using HCl in ether.

The hydrochloride was filtered off and washed with acetonitrile. The yield of 3-[2-(4-hydroxyphenoxy)-ethylamino]-1-o-methylphenoxypropanol-2 was 1.5 g. Melting point 150° C. (HCl). The structure was determined using NMR.

EXAMPLE 2

3-[2-4-hydroxyphenoxy)-ethylamino]-1-o-methoxyethylcarbonylmethoxyphenoxy-propanol-2 can be prepared in an analogous fashion starting with 1,2 epoxy-3-o-methoxyethylcarbonylmethoxyphenoxy propane and 2-(4-hdryxoyphenoxy)ethylamine.

EXAMPLE 3

A syrup containing 2% (weight per volume) of active substance was prepared from the following ingredients:

| | |
|---|---|
| 3-[2-(4-hydroxyphenoxy)-1-ethylamino]-1-o-methyl-phenoxy-propanol-2 . HCl | 2.0 g |
| Saccharine | 0.6 g |
| Sugar | 30.0 g |
| Glycerine | 5.0 g |
| Flavoring agent | 0.1 g |
| Ethanol 96% | 10.0 g |
| Distilled water | ad 100.0 ml |

Sugar, saccharine and the ethersalt were dissolved in 60 g of warm water. After cooling, glycerine and solution of flavoring agents dissolved in ethanol were added. To the mixture water was then added to 100 ml.

The above given active substance may be replaced with 3-[2-(4-hydroxyphenoxy)-1-ethylamino]-1-o-methoxyethylamin-carbonylmethoxyphenoxy-propanol or its pharmaceutically acceptable acid addition salts.

EXAMPLE 4

3-[2-(4-hydroxyphenoxy)-ethylamino-1-o-methoxyethylaminocarbonylmethoxyphenoxy]-propanol-2 hydrochloride (250 g) can be mixed with lactose (175.8 g) potatoe starch (169.7 g) and colloidal silicic acid (32 g). The mixture was moistened with a 10% solution of gelatin and was granulated through a 12 mesh sieve. After drying potato starch (160 g), talc (50 g) and magnesium stearate (5 g) were admixed and the mixture thus obtained was pressed into tablets (10.000) which contain 25 mg of substance. The tablets are sold on the market provided with a breaking score to give another dose than 25 mg or to give multiples thereof when broken.

BIOLOLGICAL EFFECTS

The agents of the present invention were tested as regards their biological properties. All compounds were thereby tested in anesthetized cats (males and females weighing 2.5–3.5 kg) pretreated with reserpine (5 mg/kg bodyweight administered intramuscularly) about 16 hours before the experiments. The animals were pretreated with reserpine in order to eliminate the endogenous sympathetic control of heart rate and vascular smooth muscle tone. The cats were anesthetized with pentobarbital (30 mg/kg bodyweight administered i.p.) and artificially ventilated with room air. A bilateral vagotomy was performed in the neck. Blood pressure was obtained from a cannulated carotid artery and heart rate was registered from a cardiotachometer, triggered by the electrocardiogram (ECG). Vascular resistance in one hind leg was recorded by an autoperfusion technique. Intrinsic beta mimetic activity on the heart was seen as increased heart rate after drug administration. The test compounds were given intravenously in logarithmically increasing doses. Before the first dose and between each of the following doses (0.012–51.2 $\mu$mol/kg) of the test compound a dose of isoproterenol (0.1 $\mu$g/kg) was injected intravenously. Blockade of the heart rate and vascular resistance response to isoproterenol was calculated for each dose and expressed as percent decrease of the response obtained when isoproterenol was injected before any dose of the test compound. Percent blockade was then plotted against the logarithm of the dose. $ED_{50}$ values i.e. doses producing a reduction of the original response to isoproterenol to 50 percent were estimated from these dose-response curves. At the end of each experiment high doses of isoprenaline were given in order to obtain the maximal heart rate response.

$\alpha$-receptor blocking activity was tested in isolated rat vas deferens. Noradrenaline administered to the organ bath induces a contraction in vas deferens by activating $\alpha$-receptors. The ability of the test compounds to inhibit this noradrenaline response was studied. The $\alpha$-receptor blocking activity was expressed as $pA_2$ values. $pA_2$ is defined as the negative logarithm of the concentration of an antagonist (in our case the test compounds) which leads to the fact that the dose of the agonist (in our case noradrenaline) has to be doubled in order to obtain the same effect of the agonist as that obtained without the antagonist present. Thus a high $pA_2$ value indicates a high α-receptor blocking activity of a compound.

The experiments demonstrate that the compounds tested are very potent β-receptor antagonists being cardioselective and with or without intrinsic β-mimetic activity. The α-receptor blocking activity is low. Results obtained in above given tests are given in Table I below.

TABLE I

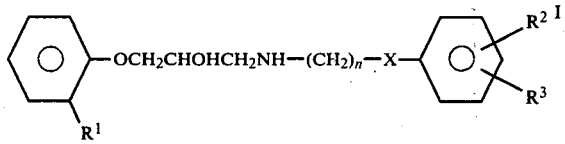

| | | Reserpinized cat | | | | |
| | | β-blockade of isoprenaline heart rate response | β-blockade of isoprenaline peripheral resistance response | Intrinsic activity | | |
| $R^1$ | $R^2$ | $ED_{50}\mu mol/kg$ | $ED_{50}\mu mol/kg$ | Δbeats/ /min. | % of iso- prenaline | $pA_2$ |
| —OCH$_2$CO— NHC$_2$H$_4$O— CH$_3$ | 4-OH | 0.05 | 1.8 | 0 | 0 | 5.5 |

We claim:

1. A compound of the formula I $$\text{[structure]}-\text{OCH}_2\text{CHOHCH}_2\text{NH}-(\text{CH}_2)_n-\text{X}-\text{[structure with }R^{2I},R^3\text{]}$$

wherein $R^1$ is $CH_3OC_2H_4NHCOCH_2$—O—, $R^2$ and $R^3$ are hydrogen, methoxy, hydroxy or hydroxymethoxy, provided that $R^2$ and $R^3$ are not both hydrogen, X is —O— or —S— and n is an integer from 2 to 4, or a therapeutically acceptable salt of such a compound.

2. The compound according to claim 1 which is 3-[2-(4-hydroxyphenoxy)-ethylamino]-1-o-methoxyethylaminocarbonylmethoxyphenoxy-propanol-2, or a therapeutically acceptable salt thereof.

3. A pharmaceutical preparation for the treatment of cardiovascular disorders in mammals which comprises at least one β-receptor blocking, phenoxyhydroxypropylamine compound according to claim 1 in association with a pharmaceutically acceptable carrier, said compound being present in an amount effective to provide in a dosage unit β-receptor blocking activity in said mammal.

4. A pharmaceutical preparation according to claim 3 wherein said compound is 3-[2-(4-hydroxyphenoxy)-ethylamino]-1-o-methoxyethylamino-carbonylmethoxyphenoxy-propanol-2, or a therapeutically acceptable salt thereof.

5. A method of treating cardiovascular disorders comprising administering to a mammal suffering from cardiovascular disorders an amount of a compound according to claim 1 effective to block the beta receptors of the heart of said mammal.

6. A method of treatment according to claim 5 wherein the compound is 3-[2-(4-hydroxyphenoxy)-ethylamino]-1-o-methoxyethylamino-carbonylmethoxyphenoxy-propanol-2, or a therapeutically acceptable salt thereof.

* * * * *

UNITED STATES PATENT AND TRADEMARK OFFICE
CERTIFICATE OF CORRECTION

PATENT NO. : 4,263,323

DATED : April 21, 1981

INVENTOR(S) : Enar Ingemar Carlsson et al.

It is certified that error appears in the above—identified patent and that said Letters Patent is hereby corrected as shown below:

First page, Add Item [30]   -- FOREIGN APPLICATION

PRIORITY DATA   October 7, 1976   Sweden   7611125-1--.

Signed and Sealed this

Ninth Day of February 1982

[SEAL]

Attest:

GERALD J. MOSSINGHOFF

Attesting Officer    Commissioner of Patents and Trademarks